United States Patent [19]

Perisse

[11] Patent Number: 5,417,569
[45] Date of Patent: May 23, 1995

[54] MULTI-ELEMENT DENTAL IMPLANT

[76] Inventor: Jean Perisse, 16, rue Fonvieille 31000, Toulouse, France

[21] Appl. No.: 211,444
[22] PCT Filed: Oct. 9, 1991
[86] PCT No.: PCT/FR91/00788
  § 371 Date: Apr. 26, 1994
  § 102(e) Date: Apr. 26, 1994
[87] PCT Pub. No.: WO93/06787
  PCT Pub. Date: Apr. 15, 1993

[51] Int. Cl.$^6$ .................. A61C 8/00; A61C 13/12; A61C 13/225
[52] U.S. Cl. .................... 433/173; 433/174; 433/177
[58] Field of Search ............ 433/172, 173, 174, 175, 433/176, 177; 623/16, 18, 20, 21, 22, 23

[56] References Cited

U.S. PATENT DOCUMENTS

| | | | |
|---|---|---|---|
| 3,589,011 | 6/1971 | Sneer | 32/10 |
| 3,708,883 | 1/1973 | Flander | 32/10 A |
| 4,259,072 | 3/1981 | Hirabayashi et al. | 433/173 |
| 4,525,145 | 6/1985 | Scheicher et al. | 433/173 |
| 4,588,381 | 5/1986 | Caracciolo | 433/173 |
| 4,609,354 | 9/1986 | Koch | 433/173 |
| 5,030,095 | 7/1991 | Niznick | 433/173 |
| 5,049,073 | 9/1991 | Lauks | 433/173 |
| 5,133,662 | 7/1992 | Metcalfe | 433/173 X |

FOREIGN PATENT DOCUMENTS

| | | |
|---|---|---|
| 0114955 | 8/1984 | European Pat. Off. |
| 0158333 | 10/1985 | European Pat. Off. |
| 1961531 | 7/1970 | Germany |
| 2305441 | 8/1974 | Germany |
| 3300764 | 7/1984 | Germany |

OTHER PUBLICATIONS

International Search Report and Annex in French and English.
International Preliminary Examination Report in French.

*Primary Examiner*—Nicholas D. Lucchesi
*Attorney, Agent, or Firm*—Sandler, Greenblum & Bernstein

[57] ABSTRACT

Suprastructure for a dental implant is provided with a false stump defining a prosthesis base plate, a shank for anchoring the false stump, with the shank including partially extending slots forming surface segments capable of radial expansion, a hollow core opening at a free end of the false stump and including a converging ramp at the free end, a series of balls positioned in the hollow core, with one of the balls abutting against the converging ramp so as to be retained thereby and to exert a spacing pressure onto the surface segments, and a screw abutting against a first ball of the series of balls to cause the balls to be moved against the converging ramp. The suprastructure can be used in combination with a tubular implantal stump adapted to be anchored in the osseous site and to accommodate the shank of the suprastructure.

20 Claims, 3 Drawing Sheets

U.S. Patent     May 23, 1995     Sheet 1 of 3     5,417,569

MULTI-ELEMENT DENTAL IMPLANT

BACKGROUND OF THE INVENTION

1. Field of the Invention

This invention relates to a multi-element dental implant for further grafting and anchoring of a dental prosthesis onto an osseous site. The invention includes the component parts of this implant as well as implant dentures made therefrom.

2. Discussion of Background Information

Dental implantology shows an increasing tendency leading to the use of multi-element implants that are composed of two separate elements, with the grafting thereof being successively effected. These multi-element implants are provided with an implantal stump composed of a tubular element which is anchored in the osseous site, and a suprastructure composed of an anchoring shank formed on the implantal stump and of a false stump that serves as a prosthesis base plate. Further, in implants such as the so-called normal implants, the false stump and the anchoring shank have collinear axes; whereas, in implants such as the so-called preangulated implants, the axes form an angle up to 20°.

First, the implant stump is anchored by screwing or any other way (DE 1,961,531, EP 0,114,955, or U.S. Pat. No. 3,708,883) in the osseous site, then the suprastructure is attached to the implantal stump by means of the anchoring shank so as to cause the false stump to take a suitable position. Actually, such anchoring in the implantal stump of the shank is achieved by two methods.

In one method the suprastructure shank is composed of a smooth bar, and is permanently sealed within the tubular implantal stump by using a cement. However, in this method, should clinical problems arise, then no removal of the suprastructure will not be possible.

In the other known anchoring method, the suprastructure shank is screwed into the implantal stump through conjugate threading and tapping as provided on these elements (See U.S. Pat. No. 3,589,011). In this method the suprastructure is releasable. However, positioning is inaccurate and hazardous, so much in the longitudinal direction (along the implant axis), because a determination, upon screwing, of the tightening stop limit proves difficult and relates to the orientation of the suprastructure about its axis, which is conditioned upon the final thread position. This angular inaccuracy forms a serious defect impairing preangulated implants, so that suitable positioning can hardly be made using this anchoring method.

SUMMARY OF THE INVENTION

The present invention intends to provide an improved multi-element implant, exempt from the above-mentioned defects. The invention aims at achieving accurate anchoring in the implantal stump (deep along the longitudinal axis and angularly about such axis) of the suprastructure while maintaining easy removal, if necessary.

Accordingly, the multi-element dental implant involved in the invention is of the type comprising a suprastructure provided with a false stump used as a prosthesis base plate and a shank for anchoring thereof, and a tubular implantal stump adapted to be anchored in the osseous site and to accommodate the suprastructure shank. In accordance with the present invention, the implant is characterized in that:

The suprastructure comprises a hollow core extending lengthwise therein, the hollow core opening at the free end of the false stump and being provided at the free end of the shank with a converging ramp,

- the suprastructure shank comprises a number of slots extending partially lengthwise therein from its free end so as to define several surface areas able to withstand radial expansion,
- several balls are accommodated within the suprastructure hollow core as a series maintaining the balls in mutual contact, the latter thereof abutting against a cone-shaped ramp of the shank so as to be retained thereby, and to exert onto surface areas of the shank a spacing pressure,
- a screw is screwed within a tapped portion of the hollow core in the vicinity of the free end of the false stump, the screw abutting against the first ball so as to cause the series of balls to be moved and fixed.

Hence, in the implant of the invention, the tubular implantal stump which is of a type known per se, is anchored in the osseous site conventionally, such as by screwing or any other way already known. The suprastructure is anchored in this implantal stump by inserting its anchoring shank therein and positioning it suitably, angularly and along the longitudinal axis. Then, a mere actuation of the upper screw will suffice to entail both the shank expansion and setting thereof inside the implantal stump. Such an operation does not modify the suprastructure angular axial position which results in the suprastructure being accurately set into a selected position. Removal of the suprastructure is achieved by simply actuating the screw counterclockwise, whereby the anchoring shank is released in the radial direction, and can be extracted.

The implant in accordance with the invention can be of the normal type, such as the shank and false stump of the suprastructure having collinear axes. Also, the implant can be preangulated so that the axes of the shank and false stump form a predetermined angle, e.g., 6°, 12° or 20°.

The invention also relates to a suprastructure as above defined for dental implant, characterized in that it comprises a hollow anchoring shank provided with a number of longitudinal slots defining several surface areas able to withstand radial expansion and the suprastructure is provided with a hollow core which is bored longitudinally therein, and comprises, at the end of the shank, a converging ramp, and, at the end of the false stump, a tapped portion. A series of balls is positioned within the hollow core between the converging ramp and a screw that is screwed into the tapped portion.

BRIEF DESCRIPTION OF THE DRAWINGS

Other features, objects and advantages of the invention will be apparent from the description as follows refering to the appended drawings, which represent two examplary embodiments, that form part of the present description.

DETAILED DESCRIPTION OF THE PREFERRED EMBODIMENT

Figure 1:
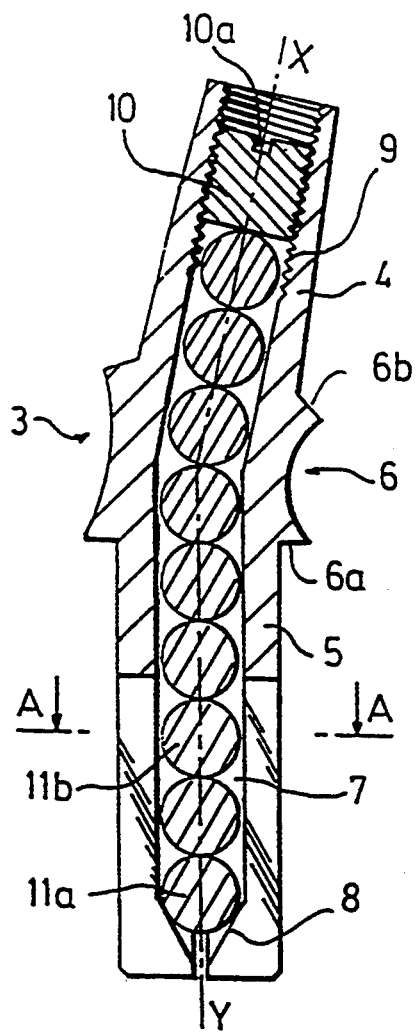
FIGS. 1 and 2 are axial cross-sections at expanded scale showing a preangulated implant in accordance with the invention, suprastructure and implantal stump thereof, respectively.
Figure 3:
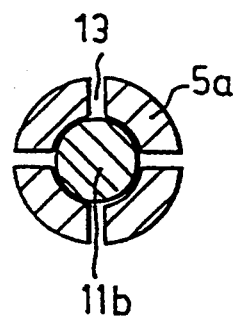
FIG. 3 is a transversal cross-section of the suprastructure through a plane AA.
Figure 2:
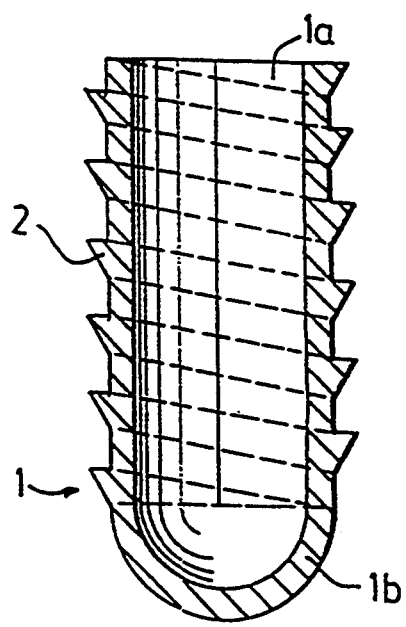

The multi-element dental implant shown for example at FIGS. 1–4 (scale approximatively 8) is a preangulated implant whereof the angle is equal to 12°. It is composed of an implantal stump 1 (FIG. 2) made for example of titanium, which takes a tubular form inclusive of a cylindrical hollow core 1a that is closed by a hemispherical bottom plate 1b. On its outer cylindrical face, this element is provided with a threading 2 to permit conventional anchoring thereof in the maxillary site.

Figure 4:
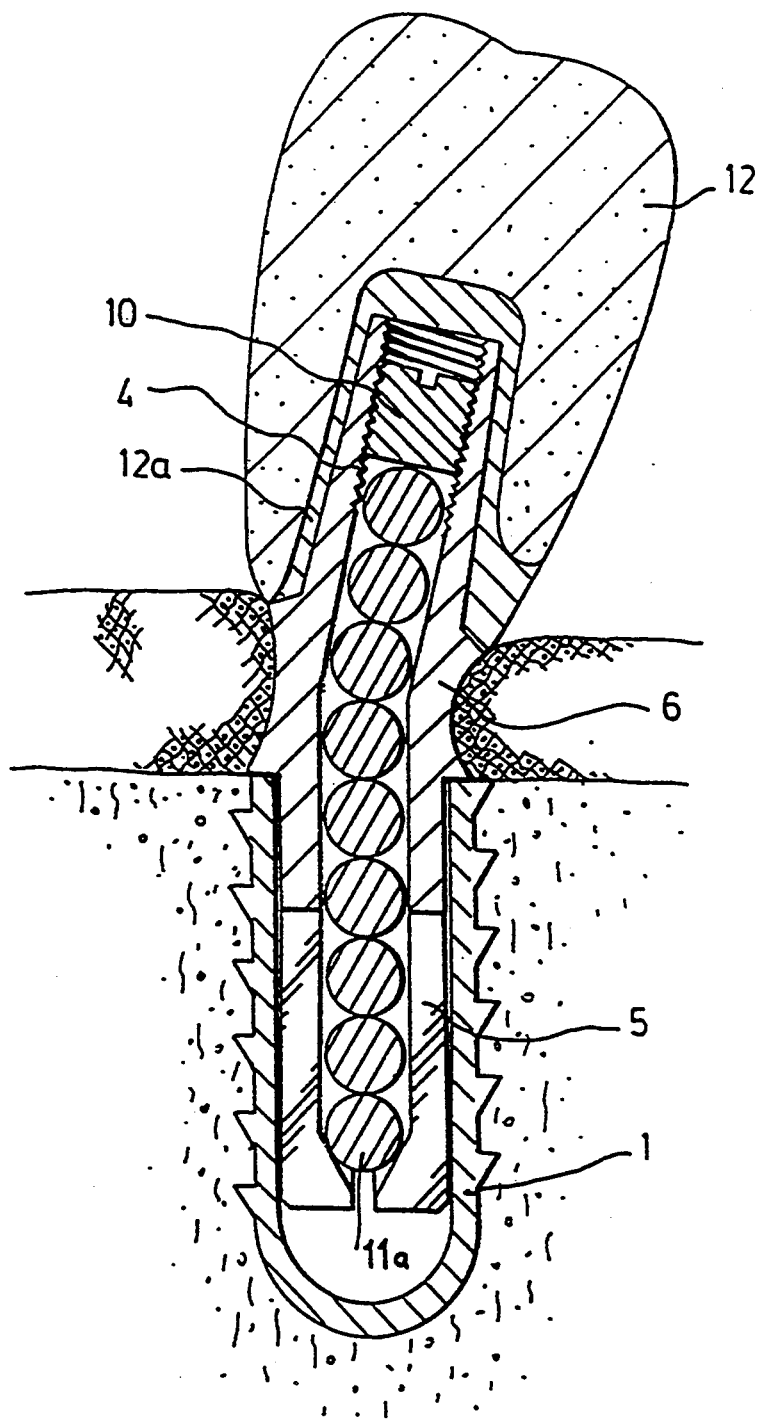
FIG. 4 is a schematic cross-section showing both the implant and prosthesis thereof as positioned on the site.

Further, the other implant element, the so-called suprastructure 3 (FIG. 1), is also made of titanium and comprises a false stump 4, shank 5 and a gingival junction 6 formed therebetween. The false stump longitudinal axis X forms together with the shank longitudinal axis Y a 12° angle. Moreover, shoulders such as 6a and 6b define the gingival junction 6. These are expected to correspond with the bone/gum interface and the gum outer surface, respectively, as shown in FIG. 4.

In the suprastructure 3 is bored in either part lengthwise longitudinal axis X, Y thereof a hollow core 7 with circular cross-section. At the free end of the shank 5, this hollow core 7 comprises a truncated ramp 8 having an apex angle thereof which is in particular, within 45° and 75°, more preferably about 60°. Additionally, the hollow core 7 is tapped to part of the length 9 thereof at the free end of its false stump.

The suprastructure shank 5 shows an outer diameter which is slightly inferior to the bore of the implantal stump 2 so as to get accommodated therein with smooth Friction. The suprastructure is divided partially lengthwise into several segments such as 5a by a number of longitudinal slots 13 (herein in the number of four) starting from the shank free end. Thus, the this shank can withstand a radial expansion in view of the resilient free motion of the segment 5a.

The hollow core 7 of the suprastructure is herein provided with several balls such as 11a, 11b formed in a series in mutual contact between the cone shaped ramp 8 and a screw 10 screwed in the tapped portion 9. These balls are given a diameter slightly smaller than that of the hollow core 7 so as to be able to move therein in the longitudinal direction. Moreover, the last ball 11a, the so-called expansion ball, comes into contact with the cone shaped ramp 8, whereas the other balls such as 11b transfer the longitudinal motion of the screw 10 thereto, the first ball of the series having contact therewith.

The screw 10 comprises a recess 10a whereby handling thereof can be made with a sharped-nosed key. Hence, the practitioner can generate a longitudinal displacement of the ball series that causes the expansion ball 11a to engage in the cone shaped ramp 8, and, consequently, cause spacing pressure to be applied onto the segments 5a. Further, the practitioner can release the same segments by performing a reversal of the operative steps.

FIG. 4 shows the implant as grafted to site with prosthesis 12 thereof. The practitioner anchors the implantal stump 1 within the osseous site of the maxillary conventionally. Thereafter, he introduces the suprastructure shank 5 in the implantal stump. Further, he axially and angularly positions the shank to bring the false stump 4 into ideal position and orientation and then he so acts on the screw 10 as to position the shank 5 in its expanded condition and set it in the implantal stump. The suprastructure can be removed, as needed, by operating the screw through a reverse operating sequence to release the shank segments.

Moreover, the prosthesis 12 is secured to the false stump 4 by any known means. In the example shown, this prosthesis is made of ceramics and comprises an internal metal cover 12a which is bonded to the false stump. Of course, the false stump of the implant can, in accordance with the invention, be adapted to provide use of any other type of prosthesis, anchoring, e.g., anchoring by means of screwing (on behalf of conjugated threading and tapping as formed onto the false stump and the prosthesis or by clipping as shown by FIG. 5).

Figure 5:
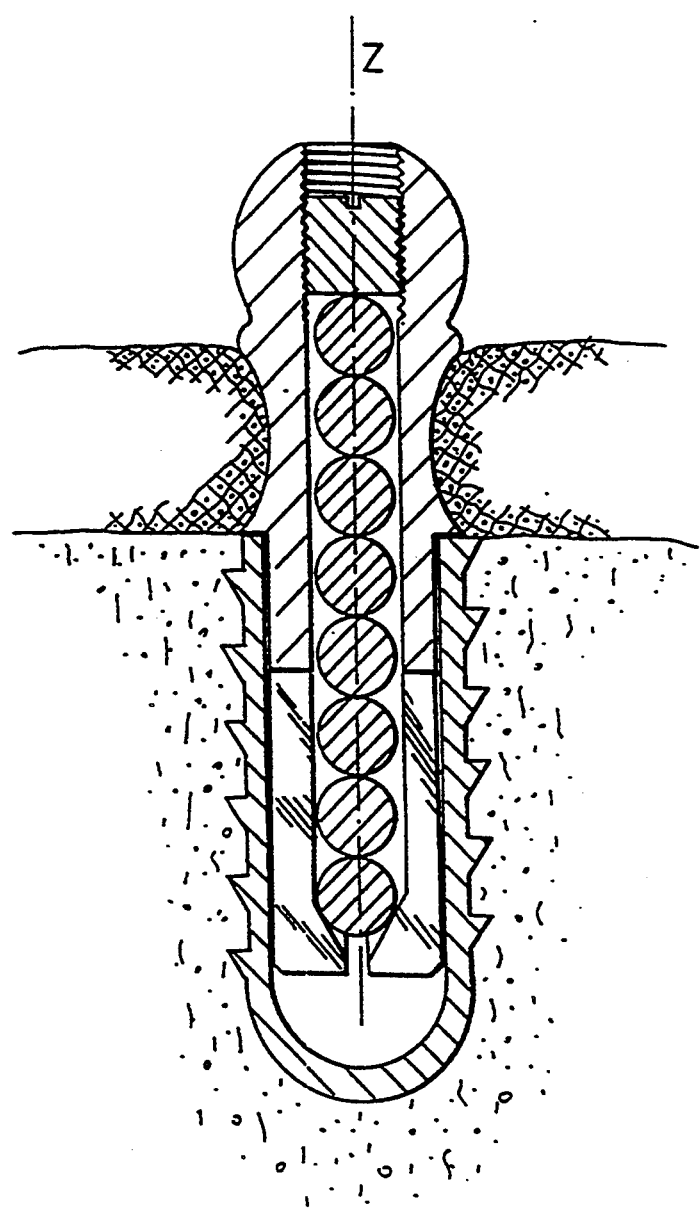
FIG. 5 is a schematic cross-section of another embodiment (normal implant) ready to accommodate a clipped prosthesis.

This FIG. 5 applies to the case of a normal implant (common axis Z shared by the shank and the false stump), whereof the false stump is equipped with the clipping head.

It should be noted that the anchored prosthesis may, upon the circumstances be provided with a channel having dimensions larger than the recess 10a of the screw to access thereat and act thereon upon the prosthesis anchoring. The prosthesis so anchored is of the fixed type although the practitioner can readily remove it at any time. The channel providing access to the screw 10 can be closed by any means to be extracted by the practitioner when required.

I claim:

1. A suprastructure for a dental implant, comprising: a false stump defining a prosthesis base plate and a shank; said shank comprising a plurality of longitudinal slots defining a plurality of surface segments capable of radial expansion; a hollow core longitudinally extending in said false stump and said shank, and comprising a converging ramp at an end of said shank and a tapped portion at an end of said false stump; a series of balls positioned within said hollow core between said converging ramp and a screw, said screw positioned within said tapped portion.

2. The suprastructure according to claim 1, comprising a prosthesis attached to said false stump.

3. The suprastructure according to claim 2, wherein said prosthesis is attached to said false stump by bonding screwing or clipping.

4. The suprastructure according to claim 1, wherein said screw comprises a recess.

5. A suprastructure, comprising:
a false stump defining a prosthesis base plate;
a shank for anchoring said false stump, said shank comprising a plurality of slots partially extending lengthwise from a free end of said shank defining a plurality of surface segments capable of radial expansion;
a longitudinally extending hollow core in said suprastructure opening at a free end of said false stump and comprising a converging ramp at said free end of said shank;
a series of balls in mutual contact positioned in said hollow core, one of said series of balls abutting against said converging ramp so as to be retained thereby and to exert a spacing pressure onto said plurality of surface segments; and an element positioned in said hollow core in a vicinity of said free end of said false stump abutting against a first ball of said series of balls to cause said series of balls to be moved into position with said one ball against said converging ramp.

6. The suprastructure according to claim 5, wherein said element comprises a screw positioned within a tapped portion of said hollow core.

7. The suprastructure according to claim 6, wherein said screw comprises a recess.

8. The suprastructure according to claim 6, wherein said converging ramp comprises a truncated ramp having an apex angle of between 45° and 75°.

9. The suprastructure according to claim 8, wherein said converging ramp comprises a truncated ramp having an apex angle of about 60°.

10. Multi-element dental implant for further grafting and anchoring of a prosthesis onto an osseous site, comprising:
 (a) a suprastructure comprising:
  (i) a false stump defining a prosthesis base plate,
  (ii) a shank for anchoring said false stump, said shank comprising a plurality of slots partially extending lengthwise from a free end of said shank defining a plurality of surface segments capable of radial expansion,
  (iii) a longitudinally extending hollow core in said suprastructure opening at a free end of said false stump and comprising a converging ramp at said free end of said shank,
  (iv) a plurality of balls serially positioned in said hollow core, each of said plurality of balls being in contact with another of said plurality of balls, one of said plurality of balls abutting against said converging ramp so as to be retained thereby and to exert a spacing pressure onto said plurality of surface segments, and
  (v) a screw positioned within a tapped portion of said hollow core in a vicinity of said free end of said false stump, said screw abutting against a first ball of the series of said plurality of balls to cause said series of balls to be moved into position; and
 (b) a tubular implantal stump adapted to be anchored in the osseous site and to accommodate said shank.

11. The dental implant according to claim 10, wherein said converging ramp comprises a truncated ramp having an apex angle of between 45° and 75°.

12. The dental implant according to claim 11, wherein said shank and said false sump have collinear axes.

13. The dental implant according to claim 11, wherein said shank and said false stump have axes defining a predetermined angle therebetween.

14. The dental implant according to claim 11, wherein said screw includes a recess.

15. The dental implant according to claim 10, wherein said converging ramp comprises a truncated ramp having an apex angle of about 60°.

16. The dental implant according to claim 15, wherein said shank and said false stump have collinear axes.

17. The dental implant according to claim 15, wherein said shank and said false stump have axes defining a predetermined angle therebetween.

18. The dental implant according to claim 10, wherein said shank and said false stump have collinear axes.

19. The dental implant according to claim 10, wherein said shank and said false stump have axes defining a predetermined angle therebetween.

20. The dental implant according to claim 10, wherein said screw includes a recess.

* * * * *

UNITED STATES PATENT AND TRADEMARK OFFICE
CERTIFICATE OF CORRECTION

PATENT NO.    : 5,417,569
DATED         : May 23, 1995
INVENTOR(S)   : Jean PERISSE It is certified that error appears in the above-indentified patent and that said Letters Patent is hereby corrected as shown below:

At column 1, line 38, delete "then no".

At column 3, line 38, change "Friction" to ---friction---.

At column 3, line 41, delete "this".

At column 4, line 14, after "prosthesis" delete ",".

At column 4, lines 50 and 51 (claim 3, lines 2 and 3), after "bonding" insert ---,---.

Signed and Sealed this

Fourteenth Day of May, 1996

BRUCE LEHMAN

*Attest:*

*Attesting Officer*     *Commissioner of Patents and Trademarks*